(12) United States Patent
Trower (10) Patent No.: US 10,195,205 B2
(45) Date of Patent: Feb. 5, 2019

(54) USES OF DUAL NK1/NK3 RECEPTOR ANTAGONISTS FOR TREATING SEX-HORMONE DISEASES

(71) Applicant: NeRRe Therapeutics Limited, Stevenage (Herts) (GB)

(72) Inventor: Mike Trower, Stevenage (GB)

(73) Assignee: NeRRe Therapeutics Limited, Stevenage, Herts (GB)

( * ) Notice: Subject to any disclaimer, the term of this patent is extended or adjusted under 35 U.S.C. 154(b) by 0 days.

(21) Appl. No.: 15/157,430

(22) Filed: May 18, 2016

(65) Prior Publication Data

US 2016/0339037 A1 Nov. 24, 2016

Related U.S. Application Data

(60) Provisional application No. 62/162,870, filed on May 18, 2015.

(51) Int. Cl.
| | | |
|---|---|---|
| *A61K 31/5383* | (2006.01) | |
| *A61K 31/436* | (2006.01) | |
| *A61K 31/40* | (2006.01) | |
| *A61K 31/4436* | (2006.01) | |
| *A61K 31/4439* | (2006.01) | |
| *A61K 31/444* | (2006.01) | |
| *A61K 31/5365* | (2006.01) | |

(52) U.S. Cl.
CPC .......... *A61K 31/5383* (2013.01); *A61K 31/40* (2013.01); *A61K 31/436* (2013.01); *A61K 31/444* (2013.01); *A61K 31/4436* (2013.01); *A61K 31/4439* (2013.01); *A61K 31/5365* (2013.01)

(58) Field of Classification Search
CPC .. A61K 31/5383; A61K 31/40; A61K 31/436; A61K 31/4436; A61K 31/4439; A61K 31/444; A61K 31/5365
See application file for complete search history.

(56) References Cited

U.S. PATENT DOCUMENTS

| 7,683,056 B2 * | 3/2010 | Alvaro | C07D 513/04 514/230.5 |
|---|---|---|---|
| 8,796,269 B2 * | 8/2014 | Craig | C07D 498/04 514/249 |
| 2002/0016283 A1 * | 2/2002 | Guttuso, Jr. | A61K 31/00 514/1 |
| 2003/0092602 A1 | 5/2003 | Leach et al. | |
| 2005/0110987 A1 | 5/2005 | Furman et al. | |
| 2006/0014818 A1 | 1/2006 | Paulini et al. | |
| 2012/0028980 A1 | 2/2012 | Boscan et al. | |

FOREIGN PATENT DOCUMENTS

| EP | 1192952 A2 | 4/2002 |
|---|---|---|
| WO | 2000059873 A1 | 10/2000 |
| WO | 2001095904 A1 | 12/2001 |
| WO | 2002/089802 A2 | 11/2002 |
| WO | 2002089802 A3 | 5/2003 |
| WO | 2004056805 A1 | 7/2004 |
| WO | 2004056799 A3 | 8/2004 |
| WO | 2005002577 A1 | 1/2005 |
| WO | 2005/097774 A1 | 10/2005 |
| WO | 2005097794 A1 | 10/2005 |
| WO | 2005/110987 A1 | 11/2005 |
| WO | 2006013050 A1 | 2/2006 |
| WO | 2006013205 A1 | 2/2006 |
| WO | 2008128891 A1 | 10/2008 |
| WO | 2011023733 A1 | 3/2011 |
| WO | 2011131571 A1 | 10/2011 |
| WO | 2012020162 A1 | 2/2012 |
| WO | 2014089019 A1 | 6/2014 |
| WO | 2015033163 A1 | 3/2015 |

OTHER PUBLICATIONS

Lee, et al., "Influence of substance-P on cultured sebocytes," Arch Dermatol Res (2008) 300:311-316.
Lehman, et al., "Minireview: kisspeptin/neurokinin B/dynorphin (KNDy) cells of the arcuate nucleus: a central node in the control of gonadotropin-releasing hormone secretion," Endocrinology 151:3479-3489, 2010).
Li, et al., "Evidence that Neurokinin B Controls Basal Gonadotropin-Releasing Hormone Secretion but Is Not Critical for Estrogen-Positive Feedback in Sheep," Neuroendocrinology 2015; 101:161-174.
Litman, et al., "The Selective Neurokinin 3 Antagonist AZD2624 Does Not Improve Symptoms or Cognition in Schizophrenia," J. Clin Psychopharmacol 2014;34: 199-204.
Lucky, et al., "Plasma Androgens in Women with Acne Vulgaris," Journal of Investigative Dermatology, 81:70-74, 1983.
Maguire, et al., "The Role of Substance P in the Central Control of Food Intake," Program: Abstracts—Orals, Posters Previews, and Poster Session, Energy Balance: Control of Adiposity and Feeding Basic. Saturday Mar. 7, 2015.
Malherbe, et al., "Characterization of RO4583298 as a novel potent, dual antagonist with in vivo activity at tachykinin NK1 and NK3 receptors," British Journal of Pharmacology, (2011) 162 929-946.
Malherbe, et al., "Tachykinin neurokinin 3 receptor antagonists: a patent review (2005-2010)," Expert. Opin. Ther. Patents (2011) 21(5):637-655.
McKinnon, et al., "Induction of the neurokinin 1 receptor by TNFα in endometriotic tissue provides the potential for neurogenic control over endometriotic lesion growth," J Clin Endocrinol Metab 98:2469-2477, 2013.
Merkley, et al, "KNDy (kisspeptin/neurokinin B/dynorphin) neurons are activated during both pulsatile and surge secretion of LH in the ewe," Endocrinology 153:5406-5414, 2012.

(Continued)

*Primary Examiner* — Robert H Havlin
(74) *Attorney, Agent, or Firm* — LeClairRyan PLLC (57) ABSTRACT

This invention relates to new use of dual NK-1/NK-3 receptor antagonists or a pharmaceutically acceptable salt thereof in the treatment of sex-hormone dependent diseases.

4 Claims, 2 Drawing Sheets

(56) References Cited

OTHER PUBLICATIONS

Millar, et al., "Current and future applications of GnRH, kisspeptin and neurokinin B analogues," Nat. Rev. Endocrinol. 9, 451-466 (2013).
Mittelman-Smith, et al, "Role for kisspeptin/neurokinin B/dynorphin (KNDy) neurons in cutaneous vasodilatation and the estrogen modulation of body temperature," PNAS Nov. 27, 2012 vol. 109, No. 48 19846-19851.
Mittelman-Smith, et al. "Neurokinin 3 Receptor-Expressing Neurons in the Median Preoptic Nucleus Modulate Heat-Dissipation Effectors in the Female Rat," Endocrinology 156:2552-2562, 2015.
Mittelman-Smith, et al., "Arcuate kisspeptin/neurokinin B/dynorphin (KNDy) neurons mediate the estrogen suppression of gonadotropin secretion and body weight," Endocrinology 153:2800-2812, 2012.
Molnar, et al, "Morphological Evidence for Enhanced Kisspeptin and Neurokinin B Signaling in the Infundibular Nucleus of the Aging Man," Endocrinology 153:5428-5439, 2012.
Navarro, et al, "Role of neurokinin B in the control of female puberty and its modulation by metabolic status," The Journal of Neuroscience, Feb. 15, 2012 32(7):2388-2397.
Navarro, et al., "Interactions between kisspeptin and neurokinin B in the control of GnRH secretion in the female rat," Am J. Physiol Endocrinol Metab 300:E202-E210, 2011.
Navarro, et al., "Regulation of gonadotropin-releasing hormone secretion by kisspeptin/dynorphin/neurokinin B neurons in the arcuate nucleus of the mouse," J. Neurosci. Sep. 23, 2009; 29(38):11859-11866.
Navarro, et al., "Regulation of NKB pathways and their roles in the control of Kiss 1 Neurons in the arcuate nucleus of the male mouse," Endocrinology 152:4265-4275, 2011.
Navarro, et al., "The integrated hypothalamic tachykinin-kisspeptin system as a central coordinator for reproduction," Endocrinology 156:627-637, 2015.
Nestor, et al., "Evidence of a role for kisspeptin and neurokinin B in puberty of female sheep," Endocrinology, 153:2756-2765, 2012).
Overgaard, et al., "Disparate changes in kisspeptin and neurokinin B expression in the arcuate nucleus after sex steroid manipulation reveal differential regulation of the two KNDy peptides in rats," Endocrinology 155:3945-3955, 2014.
Page, et al., "Excessive placental secretion of neurokinin B during the third trimester causes pre-eclampsia," Nature, vol. 405, Jun. 15, 2000, pp. 797-800.
Page, et al., "Gene regulation of neurokinin B and its receptor NK3 in late pregnancy and pre-eclampsia," Molecular Human Reproduction, vol. 12, No. 7, pp. 427-433, 2006.
Page, N.M., "Neurokinin B and pre-eclampsia: a decade of discovery," Reproductive Biology and Endocrinology 2010, 8:4.
Patak, et al., "Functional and molecular characterization of tachykinins and tachykinin receptors in the mouse uterus," Biology of Reproduction, 72, 1125-1133 (2005).
Peters, et al., "Discovery of potent, balanced and orally active dual NK1/NK3 receptor ligands," Bioorganic & Medicinal Chemistry Letters 20 (2010) 3405-3408.
Pintado, et al., "A role for tachykinins in female mouse and rat reproductive function," Biology of Reproduction, 69, 940-946 (2003).
Pinto, et al., "Ovarian steroids regulate tachykinin and tachykinin receptor gene expression in the mouse uterus," Reproductive Biology and Endocrinology, 2009; 7:77.
Porter, et al., "Neurokinin-3 receptor activation in the retrochiasmatic area is essential for the full pre-ovulatory uteinising hormone surge in ewes," J. Neuroendocrinol. Nov. 2014; 26(11):776-784.
Ramalho, et al., "Substance P antagonist improves both obesity and asthma in a mouse model," Allergy 2013; 68:48-54.
Ramaswamy, et al., "Neurokinin B stimulates GnRH release in the male monkey (*Macaca mulatta*) and is colocalized with kisspeptin in the arcuate nucleus," Endocrinology, 151:4494-4503, 2010.
Rance, et al. "Hypertrophy and increased gene expression of neurons containing neurokinin-B and substance-P messenger ribonucleic acids in the hypothalami of postmenopausal women," Endo 1991 vol. 128 No. 5, pp. 2239-2247.
Rance, et al., "Modulation of body temperature and LH secretion by hypothalamic KNDy (kisspeptin, neurokinin B and dynorphin) neurons: a novel hypothesis on the mechanism of hot flushes," Frontiers in Neuroendocrinology 34 (2013) 211-227.
Rance, et al., "Neurokinin B and the hypothalamic regulation of reproduction," Brain Res. Dec. 10, 2010; 1364:116-128.
Rance, et al.,"Postmenopausal hypertrophy of neurons expressing the estrogen receptor gene in the human hypothalamus," JCE & M 1990 vol. 71, No. 1, pp. 79-85.
Rance, N.E., "Menopause and the human hypothalamus: evidence for the role of kisspeptin/neurokinin B neurons in the regulation of estrogen negative feedback," Peptides 30 (2009) 111-122.
Renner, et al., "Neurokinin 1 receptor gene polymorphism might be correlated with recurrence rates in endometriosis," Gynecological Endocrinology, Nov. 2009; 25(11):726-733.
Ridler, et al., "Characterising the plasma-target occupancy relationship of the neurokinin antagonist GSK1144814 with PET," J Psychopharmacol 2014 vol. XX(X) 1-10.
Rometo, et al., "Changes in prodynorphin gene expression and neuronal morphology in the hypothalamus of postmenopausal women," J.Neuroendocrinol. Dec. 2008; 20(12):1376-1381.
Rotterdam eESHRE/ASRM-Sponsored PCOS Consensun Workshop Group, "Revised 2003 consensus on diagnostic criteria and long-term health risks related to polycystic ovary syndrome," Fertility and Sterility, vol. 81, No. 1, Jan. 2004, 19-25.
Ruiz-Pino, et al., "Neurokinin B and the control of the gonadotropic axis in the rat: developmental changes, sexual dimorphism, and regulation by gonadal steroids," Endocrinology 153:4818-4829, 2012.
Ruka, et al., "Regulation of arcuate neurons coexpressing kisspeptin, neurokinin B, and dynorphin by modulators of neurokinin 3 and κ-opioid receptors in adult male mice," Endocrinology 154:2761-2771, 2013.
Sandoval-Guzman, et al., "Effects of ovariectomy on the neuroendocrine axes regulating reproduction and energy balance in young cynomolgus macaques," Journal of Neuroendocrinology, 2004, vol. 16, 146-153.
Search Report and Written Opinion of PCT/EP2016/060945 dated Jun. 29, 2016.
Semple, et al., "The recent genetics of hypogonadotrophic hypogonadism—novel insights and new questions insights and new questions," Clinical Endocrinology (2010 72, 427-435.
Skorupskaite, et al., "Role of a neurokinin B receptor antagonist in the regulation of ovarian function in healthy women," Poster Abstract, Published online on Feb. 26, 2015.
Skrapits, et a., "Neuropeptide co-expression in hypothalamic kisspeptin neurons of laboratory animals and the human," Frontiers in Neuroscience, 2015, vol. 9, Article 29, pp. 1-9.
Skrupsakite, et al., "The kisspeptin-GnRH pathway in human reproductive health and disease," Human Reproduction Update, vol. 20, No. 4 pp. 485-500, 2014.
Streuli, et al., "An update on the pharmacological management of adenomyosis," Expert. Opin. Pharmacolther (2014) 15(16):2347-2360.
Struthers, et al., "Suppression of gonadotropins and estradiol in premenopausal women by oral administration of the nonpeptide gonadotropin-releasing hormone antagonist elagolix", J. Clin Endocrinol Metab, Feb. 2009, 94(2):545-551.
Tataryn IV, et al., "LH, FSH and skin temperature during the menopausal hot flash", JCE & M 1979, vol. 49, No. 1, pp. 152-154.
Taziaux, et al., "Sex differences in the neurokinin B system in the human infundibular nucleus," J. Clin Endocrinol Metab 97:E2210-E2220, 2012.
Te Beek, et al., "Pharmacokinetics and central nervous system effects of the novel dual NK1/NK3 receptor antagonist GSK1144814 in alcohol-intoxicated volunteers," Br. J. Clin Pharmacol. 75:5 1328-1339.
Topaloglu, et al., "TAC3 and TACR3 mutations in familial hypogonadotropic hypogonadism reveal a key role for Neurokinin B in the central control of reproduction," Nature Genetics, No. 3, Mar. 2009 354-358.

(56) References Cited

OTHER PUBLICATIONS

Varothai, et al., "Androgenetic Alopecia: An Evidence-Based Treatment Update," Am J Clin Dermatol (2014) 15:217-230.

Vijayan, et al., "In Vivo and In Vitro effects of substance P and neurotensin on gonadotropin and prolactin release,", Endocrinology, 105:64, 1979).

Wakabayashi, et al., "Neurokinin B and dynorphin A in kisspeptin neurons of the arcuate nucleus participate in generation of periodic oscillation of neural activity driving pulsatile gonadotropin-releasing hormone secretion in the goat," The Journal of Neuroscience, Feb. 24, 2010, 30(8):3124-3132.

Yamamura, et al., "Effects of intravenous administration of neurokinin receptor subtype-selective agonists on gonadotropin-releasing hormone pulse generator activity and luteinizing hormone secretion in goats," J. Reprod. Dev. 61:20-29, 2015.

Yang, et al., "Uncovering novel reproductive defects in neurokinin B receptor null mice: closing the gap between mice and men," Endocrinology 153:1498-1508, 2012.

Young, et al., "TAC3 and TACR3 defects cause hypothalamic congenital hypogonadotropic hypogonadism in humans," J Clin Endocrinol. Metab, May 2010 95(5):2287-2295.

Abel, et al,, "Stereologic study of the hypothalamic infundibular nucleus in young and older women", The Journal of Comparative Neurology, 424:679-688 (2000).

Abel, et al., "The effects of hormone replacement therapy on hypothalamic neuropeptide gene expression in a primate model of menopause," JCE & M 1999 vol. 84, No. 6, pp. 2111-2118.

Arisawa, et al., "Stimulatory role of substance P on gonadotropin release in ovariectomized rats," Neuroendocrinology, 1990; 51:523-529.

Azziz, et al, "Positions statement: criteria for defining polycystic ovary syndrome as a predominantly hyperandrogenic syndrome: an Androgen Excess Society guideline," J. Clin Endocrinol. Metab 91: 4237-4245, 2006.

Bardia, et al. "Pilot evaluation of Aprepitant for the treatment of hot flashes," Supportive Cancer Therapy, vol. 3, No. 4, 240-246, 2006.

Biissantz et al., "Identification of Crucial Amino Acid in the Helix Position 6.51 of Human tachkinin Neurokininn 1 and 3 Receptor contributing to the insurmountable Mode of antagonism by dual NK1/NK3 Antagonists," J. Med. Chem. 2012, 55, 5061-5076.

Billings, et al., "Neurokinin B acts via the neurokinin-3 receptor in the retrochiasmatic area to stimulate luteinizing hormone secretion in sheep," Endocrinology, 151:3836-3846, 2010).

Biran, et al., "Direct Regulation of Gonadotropin Release by Neurokinin B in Tilapia (*Oreochromis niloticus*)," Endocrinology 155:1-12, 2014.

Borsay, et al., "Hypophysiotropic gonadotropin-releasing hormone projections are exposed to dense plexuses of kisspeptin, neurokinin B and substance p immunoreactive fibers in the human: a study on tissues from postmenopausal women" Neuroendocrinology 2014; 100:141-152.

Brown, et al., "Gonadal steroid regulation of substance P (SP) and SP-encoding messenger ribonucleic acids in the rat anterior pituitary and hypothalamus," Endocrynology 126:330-340, 1990.

Brylla, et al., "Coexpression of preprotachykinin A and B transcripts in the bovine corpus luteum and evidence for functional neurokinin receptor activity in luteal endothelial cells and ovarian macrophages," Regulatory Peptides, 125 (2005) 125-133.

Burke, et al., "Coexpression of dynorphin and neurokinin B immunoreactivity in the rat hypothalamus: Morphologic evidence of interrelated function within the arcuate nucleus," The journal of Comparative Neurology 498:712-726 (2006).

Candenas, et al., "Changes in the expression of tachykinin receptors in the rat uterus during the course of pregnancy,", Biology of Reproduction, 65, 538-543 (2001).

Casper, et al., "Menopausal flushes: a neuroendocrine link with pulsatile luteinizing hormone secreation," Science, vol. 205, 1979, pp. 823-825.

Casper, et al., "Menopausal flushes: effect of pituitary gonadotropin desensitization by a potent luteinizing hormone-releasing factor agonist," JCE & M, 1981, vol. 53 No. 5, pp. 1056-1058.

Catalani, et al., "Identification of novel NK1/NK3 dual antagonists for the potential treatment of schizophrenia," Bioorganic & Medicinal Chemistry Letters, 21 (2011) 6899-6904.

Chawla, et al., "Localization of neurons expressing substance P and neurokinin B gene transcripts in the human hypothalamus and basal forebrain", The Journal of Comparative Neurology, 384:429-442 (1997).

Cheng, et al., "The kisspeptin/neurokinin B/dynorphin (KNDy) cell population of the arcuate nucleus: sex differences and effects of prenatal testosterone in sheep," Endocrinology 151:301-311, 2010.

Ciofi, et al., "Presence of nuclear androgen receptor-like immunoreactivity in neurokinin B-containing neurons of the hypothalamic arcuate nucleus of the adult male rat," Neuroscience Letters 182 (1994) 193-196.

Dacks, et al., "Activation of neurokinin 3 receptors in the median preoptic nucleus decreases core temperature in the rat," Endocrinology 152:4894-4905, 2011.

Dawson, et al., "Progress in the development of neurokinin 3 modulators for the treatment of schizophrenia: molecule development and clinical progress," Future Med Chem (2013) 5(13), 1525-1546.

De Croft, et al., "Neurokinin B activates arcuate kisspeptin neurons through multiple tachykinin receptors in the male mouse," Endocrinology 154:2750-2760, 2013.

Dellovade, et al., "Estrogen regulation of neurokinin B gene expression in the mouse arcuate nucleus is mediated by estrogen receptor alpha," Endocrinology 145(2):736-742 2004.

Ebede, et al., "Hormonal Treatment of Acne in Women," J Clin Aesthetic Dermatol. 2009;2(12):16-22.

Endo, et al., "Effects of senktide, a neurokinin 3 receptor agonist, on luteinizing hormone secretion and follicular development in anestrous Shiba goats: a pilot study," BMC Research Note 2014, 7:773.

Escobar-Morreale, et al., "Epidemiology, diagnosis and management of hirsutism: a consensus statement by the Androgen Excess and Polycystic Ovary Syndrome Society," Human Reproduction Update vol. 18, No. 2, pp. 146-170, 2012.

Fleury, et al., "A pharmacokinetic-pharmacodynamic model for cardiovascular safety assessment," Journal of Pharmacological and Toxicological Methods 63 2011) 123-133.

Francou, et al., "Normosmic congenital hypogonadotropic hypogonadism due to TAC3/TACR3 mutations: characterization of neuroendocrine phenotypes and novel mutations," PLoS ONE 6(10:e25614.

Fukami, et al., "Hypothalamic dysfunction in a female with isolated hypogonadotropic hypogonadism and compound heterozygous TACR3 mutations and clinical manifestation in her heterozygous mother," Horm Res Paediatr. 2010;73:477-481.

Garcia-Galiano, et al., "Kisspeptin signaling is indispensable for neurokinin B, but not glutamate, stimulation of gonadotropin secretion in mice," Endocrinology 153:316-328, 2012.

Garcia-Ortega, et al., Expression of neurokinin B/NK3, Human Reproduction, vol. 0, No. 0 pp. 1-11, 2014.

George, et al., "The Neurokinin B Receptor Antagonist AZD4901 Decreases LH and Testosterone Secretion in Women with PCOS: A Randomised, Double-Blind, Placebo-Controlled Clinical Trial," Ptogram: Abstracts—Orals, Poster Previews, and Posters Session: OR27—Hyperandrogenic Ovarian Dysfunction Basic/Clinica, Saturday Mar. 7, 2015.

Gianetti, et al. "TAC3/TACR3 mutations reveal preferential activation of gonadotropin-releasing hormone release by neurokinin B in neonatal life followed by reversal in adulthood," J. Clin. Endocrinol Metab 95; 2857-2867, 2010).

Gollnick, et al., "Management of acne: a report from a Global Alliance to Improve Outcomes in Acne," J. Am Acad. Dermatol. vol. 49, No. 1, 2003 pp. S1-S37.

Guran, et al., "Hypogonadotropic hypogonadism due to a novel missense mutation in the first extracellular loop of the neurokinin B receptor," J Clin Endocrin Metab 94:3633-3639, 2009.

Hanessian, et al., "Design and synthesis of potential dual NK1/NK3 receptor antagonists," Bioorg. Med. Chem. Lett 24 (2014) 510-514.

(56) References Cited

OTHER PUBLICATIONS

Hanessian, et al., "Design, Synthesis, and Optimization of Balanced Dual NK1/NK3 Receptor Antagonists," ACS Med. Chem. Lett. 2014, 5, 550-555.
Hofmann, et al., "Discovery of potent, balanced and orally active dual NK1/NK3 receptor ligands", Bioorganic & Medicinal Chemistry Letters 20 (2010) 3405-3408.
Hoveyda, et al., "Discovery and optimization of novel antagonists to the human neurokinin-3 receptor for the treatment of sex-hormone disorders (Part I)," J. Med. Chem. 2015, 58, 3060-3082.
Hrabovszky, et al, "Low degree of overlap between kisspeptin, neurokinin B, and dynorphin immunoreactivities in the infundibular nucleus of young male human subjects challenges the KNDy neuron concept," Endocrinology 153:4978-4989, 2012.
Hrabovszky, et al., "Substance P immunoreactivity exhibits frequent colocalization with kisspeptin and neurokinin B in the human infundibular region," PLoS ONE 8(8): e72369 2013.
Hrabovszky, et al., "The kisspeptin system of the human hypothalamus: sexual dimorphism and relationship with gonadotropin-releasing hormone and neurokinin B neurons," European Journal of Neuroscience, vol. 31, pp. 1984-1998, 2010.
Jayasena, et al., "Neurokinin B Administration Induces Hot Flushes in Women," Sci. Rep. 5, 8466: 1-7 (2015).
Karagiannides, et al., "Substance P (SP)-Neurokinin-1 Receptor (NK-1R) Alters Adipose Tissue Responses to High-Fat Diet and Insulin Action," Endocrinology 152:2197-2205, 2011.
Karjewski, et al., "Forebrain projections of arcuate neurokinin B neurons demonstrated by anterograde tract-tracing and monosodium glutamate lesions in the rat," Neuroscience Mar. 17, 2010; 166(2):680-697.
Karsch, F.J., "Central actions of ovarian steroids in the feedback regulation of pulsatile secretion of luteinizing hormone," Ann. Rev. Physiol., 1987, 49:365-82.
Kinsey-Jones, et al., "The inhibitory effects of neurokinin B on GnRH pulse generator frequency in the female rat," Endocrinology 153:307-315, 2012.
Krajewski, et al., "Morphologic evidence that neurokinin B modulates gonadotropin-releasing hormone secretion via neurokinin 3 receptors in the rat median eminence," The Journal of Comparative Neurology, 489:372-386 (2005).
Larsen, P. J., "Distribution of substance P-immunoreactive elements in the preoptic area and the hypothalamus of the rat," The Journal of Comparative Neurology, 316:287-313 (1992).
Lasaga, et al., "Tachykinins and the hypothalamo-pituitary-gonadal axis_An update," Peptides 32 (2011) 1972-1978.
Communication pursuant to Rules 161(1) and 162 EPC pertaining to corresponding European Patent Application No. 16723109.5 dated Jan. 3, 2018.
Sloan et al., "Methodologic Lessons Learned From Hot Flash Studies," J. Clin. Oncol. 19(23):4280-90 (2001).
Archer et al., "A double-blind, randomly assigned, placebo-controlled study of desvenlafaxine efficacy and safety for the treatment of vasomotor symptoms associated with menopause," Am J Obstet Gynecol. 200(2):172.e1-10 (2009).
Maclennan et al., "Oral oestrogen and combined oestrogen/progestogen therapy versus placebo for hot flushes," Cochrane Database Syst Rev. 18;(4):CD002978 (2004).
Pinkerton et al., "Relief of vasomotor symptoms with the tissue-selective estrogen complex containing bazedoxifene/conjugated estrogens: a randomized, controlled trial," Menopause. 16(6):1116-24 (2009).
Bouchard et al., "Randomized placebo- and active-controlled study of desvenlafaxine for menopausal vasomotor symptoms," Climacteric 15(1):12-20 (2012).
Bertrand et al., "Capsaicin Increases Airflow Resistance in Guinea Pigs In Vivo by Activating both NK2 and NK1 Tachykinin Receptors," Am. Rev. Respir. Dis.148:909-914 (1993).
Rumsey and Kerns, "Combined Tachykinin NK1, NK2, and NK3 Receptor Antagonists," in Tachykinins, Holzer (ed.), Springer-Verlag (Heidelberg, 2004).
Daoui et al., "Involvement of Tachykinin NK3 Receptors in Citric Acid-induced Cough and Bronchial Response in Guinea Pigs," Am. J. Respir. Crit. Care Med. 158:42-48 (1998).
EMEND (aprepitant) capsules, for oral use prescription label. Revised: Dec. 2012. Reference ID: 3283529.
Teixeira et al., "Effects of central administration of tachykinin receptor agonists and antagonists on plus-maze behavior in mice," Eur J Pharmacol. 5;311(1):7-14 (1996).
Schwarz & Ackenheil, "The role of substance P in depression: therapeutic implications," Dialogues Clin Neurosci. 4(1):21-9 (2002).
Stratton et al., "Anxiolytic activity of tachykinin NK2 receptor antagonists in the mouse light-dark box," Eur J Pharmacol. 250(3):R11-2 (1993).
Louis et al., "Additional evidence for anxiolytic- and antidepressant-like activities of saredutant (SR48968), an antagonist at the neurokinin-2 receptor in various rodent-models," Pharmacol Biochem Behav. 89(1):36-45 (2008).
Ribeiro et al., "Tachykinin NK(3)receptor involvement in anxiety," Neuropeptides 33(2):181-8 (1999).
Panocka et al., "Antidepressant-type effect of the NK3 tachykinin receptor agonist aminosenktide in mouse lines differing in endogenous opioid system activity," Peptides 22(7):1037-42 (2001).
Regoli et al, "Neuropeptides (Neurokinins, Bombesin, Neurotensin, Cholecystokinins, Opioids) and Smooth Muscle," in Pharmacology of Smooth Muscle, Szekeres & Papp (ed.), Springer-Verlag (Heidelberg, 1994).
Patacchini et al., "Tachykinin NK1 and NK2 receptors mediate inhibitory vs excitatory motor responses in human isolated corpus cavernosum and spongiosum," Br J Pharmacol. 135(6):1351-4 (2002).
Rameshwar & Gascón, "Hematopoietic modulation by the tachykinins," Acta Haematol. 98(2):59-64 (1997).
Scholzen et al., "Cutaneous allergic contact dermatitis responses are diminished in mice deficient in neurokinin 1 receptors and augmented by neurokinin 2 receptor blockage," FASEB J. 18(9):1007-9 (2004).
Garcia-Recio and Gascón, "Biological and Pharmacological Aspects of the NK1-Receptor," Biomed Res Int. 2015:495704 (2015).
Archer et al., "A randomized, double-blind, placebo-controlled study of the lowesteffective dose of drospirenone with 17A-estradiol for moderate to severe vasomotor symptoms in postmenopausal women," Menopause: The Journal of The North American Menopause Society 21(3):227-235 (2014).
BRISDELLE® (paroxetine) capsules, for oral use prescription label. Revised Jan. 2017. Reference ID: 4036886.
Simon et al., "Low-dose paroxetine 7.5 mg for menopausal vasomotor symptoms: Two randomized controlled trials," Menopause: The Journal of The North American Menopause Society 20(10):1027-1035 (2013).
Foulon et al., "Nk1 and NK2 Receptors Mediate Tachykinin and Resiniferatoxin-Induced Bronchospasm in Guinea Pigs," Am Rev Respir Dis 148:915-921 (1993).
Ng, "Chapter 5: Drug Development and Preclinical Studies," Drugs From Discovery to Approval, Second Edition, John Wiley & Sons, Inc., pp. 136-175 (2009).
Ng, "Chapter 6: Clinical Trials," Drugs From Discovery to Approval, Second Edition, John Wiley & Sons, Inc., pp. 176-207 (2009).
Paul et al., "How to Improve R&D Productivity: The Pharmaceutical Industry's Grand Challenge," Nature Review/Drug Discovery 9:203-214 (2010).
Savoie et al., "Involvement of NK1 and NK2 Receptors in Pulmonary Responses Elicited by Non-Adrenergic, Non-Cholinergic Vagal Stimulation in Guinea-Pigs," J. Pharm.Pharmacol. 47:914-920 (1995).
DiMasi et al., "Trends in Risks Associated With New Drug Development: Success Rates for Investigational Drugs," Clinical Pharmacology & Therapeutics 87(3):272-277 (2010).

* cited by examiner

Table 1. Free and total testosterone levels in HVs from single ascending dose study

| Treatment | Timepoint | n | Free testosterone (pmol/L) | | | Total testosterone (nmol/L) | | |
|---|---|---|---|---|---|---|---|---|
| | | | Mean | SD | Mean % change from baseline | Mean | SD | Mean % change from baseline |
| Placebo | Day 1 pre-dose | 12 | 48.5 | 15.0 | | 23.5 | 6.8 | |
| | 24 h post dose | 12 | 51.4 | 11.3 | 6.0 | 24.3 | 6.6 | 3.4 |
| 10 mg | Day 1 pre-dose | 2 | 51.0 | 4.4 | | 18.4 | 6.3 | |
| | 24 h post dose | 2 | 46.3 | 18.8 | -9.2 | 21.0 | 10.3 | 14.1 |
| 30 mg | Day 1 pre-dose | 3 | 42.2 | 5.5 | | 15.9 | 2.0 | |
| | 24 h post dose | 3 | 50.4 | 10.0 | 19.4 | 16.7 | 4.4 | 5.0 |
| 60 mg | Day 1 pre-dose | 10 | 44.3 | 17.7 | | 22.0 | 7.1 | |
| | 24 h post dose | 10 | 43.9 | 14.5 | -0.9 | 23.7 | 5.8 | 7.7 |
| 120 mg | Day 1 pre-dose | 10 | 41.7 | 12.3 | | 23.1 | 6.1 | |
| | 24 h post dose | 10 | 38.0 | 17.9 | -8.9 | 18.9 | 7.9 | -18.2 |
| 160 mg | Day 1 pre-dose | 9 | 49.2 | 14.3 | | 22.6 | 6.9 | |
| | 24 h post dose | 9 | 31.1 | 13.0 | -36.8 | 14.6 | 8.5 | -35.4 |
| Individualized dose 160-250 mg | Day 1 pre-dose | 8 | 47.2 | 9.1 | | 20.9 | 5.7 | |
| | 24 h post dose | 8 | 26.9 | 15.7 | -43.0 | 12.9 | 7.2 | -38.3 |

Key: SD = standard deviation

*FIG. 1*

Table 2. Free and total testosterone levels in HVs from repeat dose study

| Treatment | Timepoint | n | Free testosterone (pmol/L) | | | Total testosterone (nmol/L) | | |
|---|---|---|---|---|---|---|---|---|
| | | | Mean | SD | Mean % change from baseline | Mean | SD | Mean % change from baseline |
| Placebo (Cohorts 1 & 2) N=5 | Day 1 (PD) | 5 | 49.2 | 20.7 | | 18.0 | 5.1 | |
| | Day 15 | 5 | 56.4 | 10.8 | 14.6 | 18.9 | 3.3 | 5.0 |
| 30 mg N=5 | Day 1 (PD) | 5 | 48.6 | 6.9 | | 22.6 | 5.5 | |
| | Day 15 | 5 | 53.4 | 15.4 | 9.9 | 21.6 | 3.4 | -4.4 |
| 90 mg N=9* | Day 1 (PD) | 7 | 48.7 | 10.4 | | 19.9 | 5.6 | |
| | Day 15 | 7 | 55.0 | 13.0 | 12.9 | 20.0 | 6.1 | 0.5 |
| Placebo (Cohort 3) N=3 | Day-1 | 3 | 62.8 | 7.0 | | 23.4 | 1.7 | |
| | Day 14 (PD) | 3 | 52.1 | 16.6 | -17.0 | 19.8 | 1.0 | -15.4 |
| 200 mg N=15** | Day-1 | 13 | 46.0 | 12.1 | | 22.3 | 4.6 | |
| | Day 14 (PD) | 13 | 25.4 | 9.8 | -44.8 | 12.7 | 4.0 | -43.0 |

Key: SD = standard deviation; * two subjects in the 90 mg dose arm were dose reduced between baseline and Day 5 and have been removed from the analysis to avoid confounding the data; ** two subjects in the 200 mg dose arm were dose-reduced between baseline and Day 14 (data removed)

*FIG. 2*

USES OF DUAL NK1/NK3 RECEPTOR ANTAGONISTS FOR TREATING SEX-HORMONE DISEASES

This non-provisional application claims priority to and the benefit of U.S. Provisional Application No. 62/162,870 filed on May 18, 2015, incorporated herein by reference in its entirety.

FIELD OF THE INVENTION

This invention relates to a method of treatment of sex-hormone dependent diseases, in a mammal, for which gonadotropin suppression and/or androgen suppression is desired. Gonadotropin and/or androgen suppression is achieved according to this invention by administration of a dual neurokinin-1 (NK-1) receptor antagonist and neurokinin-3 (NK-3) receptor antagonist (herein called dual NK-1/NK-3 receptor antagonists). Suitable dual NK-1/NK-3 receptor antagonists useful in this invention are represented by the compounds described herein.

BACKGROUND OF THE INVENTION

Androgens are generally known as the male sex hormones. The androgenic hormones are steroids, which are produced in adult males by the testes and adult females by ovarian theca cells; and a lesser amount by the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern The endogenous steroidal androgens include testosterone and dihydrotestosterone ("DHT"). Testosterone is the principal steroid secreted by the testes and is the primary circulating androgen found in the plasma of adult males. Under normal physiological circumstances males produce much more testosterone than females. Testosterone is converted to DHT by the enzyme 5-alpha-reductase in many peripheral tissues. DHT is thus thought to serve as the intracellular mediator for most androgen actions.

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle stimulating hormone (FSH). LH released from the pituitary gland is primarily responsible for the regulation of gonadal steroid production in both sexes, whereas FSH regulates spermatogenesis in males and follicular development in females.

It has been found that androgen and/or gonadotropin suppression or abrogation may result in beneficial effects, in a number of diseases and clinical applications, in males and in females.

In men these diseases or disorders, include, but are not limited to benign prostatic hyperplasia (BPH), metastatic prostatic carcinoma, breast cancer, testicular cancer, androgen dependent acne, hypertrichosis, seborrhoea, male pattern baldness and precocious puberty in boys.

In women, androgen and/or gonadotropin suppression or abrogation, has been shown to be therapeutic in clinical settings, such as, for example, in treating Polycystic Ovarian Syndrome (PCOS), endometriosis, adenomyosis, uterine fibroids, heavy menstrual bleeding, hirsutism, androgen dependent acne, seborrhoea, female androgenetic alopecia and hypertrichosis, gonadal steroid-dependent neoplasm (breast cancer, ovary cancer, etc.), gonadotropin-producing pituitary adenoma, premenstrual syndrome and sterility (e.g. assisted reproductive techniques such as in vitro fertilization). Other related conditions affecting women are pre-eclampsia and pregnancy prevention (contraception), and for both sexes, hidradenitis suppurativa and hot flushes.

As is the case in male and female subjects, however, gonadotropin and androgen suppression (also called androgen deprivation) is accompanied by a variety of undesirable clinical conditions and symptoms. For males receiving gonadotrophin releasing hormone (GnRH) agonists these initially cause a flare of increased androgen production that in patients with sex-hormone sensitive cancers may cause a short term increase in tumour growth and if the cancer has spread to the bone it may result in pain. These agents are also injected so there could be soreness, swelling and redness at the injection site. Other side effects that are also associated with GnRH antagonists are for example reduced or absent libido, impotence, shrinkage of testicles and penis, hot flushes, breast tenderness or growth of breasts, osteoporosis, anemia, cognitive reduction, muscle mass loss, weight gain, fatigue, elevated cholesterol and depression.

For male subjects administered 5-alpha-reductase inhibitors side effects are sexual in nature for example erectile dysfunction, decreased libido, reduced ejaculate and breast enlargement or tenderness. These drugs can also lower levels of Prostate-Specific Antigen (PSA) thereby interfering with the results of this analyte utilised to detect prostate cancer. Male and female subjects may also experience with spironolactone breast tenderness, menstrual irregularities (females only), fatigue, dizziness, confusion, nausea and vomiting, headache, hypotension, diarrhoea and possibly hyperkalemia. Cyproterone acetate can cause oligomenorrhea (females only), melasma, fluid retention, nausea and vomiting; this drug is also in rarer cases associated with liver hepatotoxicity and clotting disorders. Flutamide administration may lead to breast tenderness, gastrointestinal upset, hot flashes, and decreased libido; it has a serious potential side-effect of hepatotoxicity. Females taking combined oral contraceptives may experience metrorrhagia, nausea, vomiting, breast tenderness and headaches; and more rarely blood clots, myocardial infarctions, stroke, abnormal lipid indices, glucose intolerance and hypertension.

New innovative approaches are urgently needed at both the basic science and clinical levels to develop compositions and treatment regimens, which provide the beneficial effects of androgen and/or gonadotropins suppression or abrogation, without the deleterious side-effects associated with the current treatments for sex-hormone dependent diseases.

Tachykinins belong to a family of short peptides that are widely distributed in the mammalian central and peripheral nervous system (Bertrand and Geppetti, Trends Pharmacol. Sci. 17: 255-259 (1996)). They share the common C-terminal sequence Phe-Xaa-Gly-Leu-Met-NH2. The three major tachykinins are Substance P (SP), Neurokinin A (NKA) and Neurokinin B (NKB) with preferential affinity for respectively three distinct receptor subtypes, termed NK-1, NK-2, and NK-3.

Compounds showing selective affinity simultaneously to both NK-1 and NK-3 receptors namely dual NK-1/NK-3 receptor antagonists are being developed for the treatment of both schizophrenia and substance abuse disorders.

Prior to the present invention, however it has not been disclosed or suggested that a dual NK-1/NK-3 receptor antagonist according to the present invention would be useful in the treatment of sex-hormone dependent diseases in which decreased levels of androgens and gonadotropins are desired.

SUMMARY OF THE INVENTION

The present invention relates to the novel use of dual NK-1/NK-3 receptor antagonists to achieve gonadotropin and/or androgen suppression in mammals. According to this invention, dual NK-1/NK-3 receptor antagonists are administered for the treatment of diseases which are caused by abnormal levels of androgens, particularly testosterone. The compounds described herein by reference are particularly useful according to this invention.

Thus, the solution provided by the present invention is the use of dual NK-1/NK-3 receptor antagonists in the treatment of sex-hormone dependent diseases.

Specifically, in a first aspect, the invention provides a method of treatment of sex-hormone dependent diseases comprising administering to a human in need thereof an effective amount of dual NK-1/NK-3 receptor antagonists or a pharmaceutically acceptable salt thereof.

In a further aspect thereof, the invention provides the use of dual NK-1/NK-3 receptor antagonists or a pharmaceutically acceptable salt thereof for the manufacture of a medicament for the treatment of sex-hormone dependent diseases.

In a yet further aspect thereof, the invention provides dual NK-1/NK-3 receptor antagonists or a pharmaceutically acceptable salt thereof for use in the treatment of sex-hormone dependent diseases.

In a yet further aspect thereof, the invention provides a method for providing oral contraception, said method comprising administering to the patient an effective amount of dual NK-1/NK-3 receptor antagonists.

In a further aspect of the invention there is provided the use of dual NK-1/NK-3 receptor antagonists for the production of a drug for oral contraception.

DETAILED DESCRIPTION OF THE INVENTION

Surprisingly, it has now been found that dual NK-1/NK-3 receptor antagonists are effective in suppressing gonadotropin and/or androgen production/secretion, specifically in suppressing the production of LH and/or testosterone in mammals. Suppression of gonadotropin production/secretion results in the suppression of androgen production/secretion. Thus, the instant invention is in a method of treatment of sex-hormone dependent diseases which are affected, or exacerbated by, elevated and/or abnormal levels of gonadotropins and/or androgens. Specifically, the invention relates to a method of suppressing gonadotropin and/or androgen blood levels by administering an effective amount of a dual NK-1/NK-3 receptor antagonist. The compounds defined herein exhibit the ability to suppress gonadotropin and/or androgen production, and in particular, are effective in reversibly lowering blood levels of LH and the androgen testosterone.

Definitions

All numbers expressing quantities, percentages or proportions, and other numerical values used in the specification and claims, are to be understood as being modified in all instances by the term "about."

It should be understood that the terms "a" and "an" as used herein refer to "one or more" of the enumerated components. It will be clear to one of ordinary skill in the art that the use of the singular includes the plural unless specifically stated otherwise.

The term "sex hormone-dependent disease" as used herein means a disease which is exacerbated by, or caused by, excessive, inappropriate or unregulated sex hormone production.

Example of such diseases in men include but are not limited to benign prostatic hyperplasia (BPH), metastatic prostatic carcinoma, testicular cancer, breast cancer, androgen dependent acne, seborrhoea, hypertrichosis, male pattern baldness and in boys precocious puberty. Example of such diseases in women include but not limited to endometriosis, adenomyosis, abnormal puberty, uterine fibrosis, heavy menstrual bleeding, hormone-dependent cancers (ovarian cancer, breast cancer), hyperandrogenism, hirsutism, hypertrichosis, female androgenetic alopecia, androgen dependent acne, seborrhoea, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor) and osteoporosis. In women other examples are pre-eclampsia and for both sexes, hidradenitis suppurativa and hot flushes.

As used herein "a dual NK-1/NK-3 receptor antagonist" refers to a compound that shows in a single molecule simultaneously affinity to both NK-1 and NK-3 receptors.

The term "androgen" is used herein to mean steroids that encourage the development of male sex characteristics and include the steroid derivatives of androstane including testosterone, dihydrotestosterone, androstenedione, and analogs.

As used herein, "gonadotropin suppression" refers to the reduction in the production or synthesis of one or more naturally occurring gonadotropins, including lutinizing hormone and follicle-stimulating hormone.

As used herein, "androgen suppression" refers to an effective amount of a dual NK-1/NK-3 receptor antagonist, which will cause a decrease in the in vivo levels of the androgen to normal or sub-normal levels, when given to a patient for the prophylaxis or treatment of a disease state which is exacerbated by, or caused by, excessive or unregulated androgen production.

As used herein, the term "hot flushes" is interchangeable with the term "hot flashes" and with the term "vasomotor symptoms" and intended to have the same meaning.

As used herein, the terms "treatment," "treating," and the like, refer to obtaining a desired pharmacologic, physiologic, dermatologic or cosmetic effect. The effect may be prophylactic in terms of completely or partially preventing a condition or disease or disorder or symptom thereof and/or may be therapeutic in terms of a partial or complete cure for a condition or disease or disorder and/or adverse symptom or effect attributable to the condition or disease or disorder.

"Treatment," thus, for example, covers any treatment of a condition or disease in a mammal, particularly in a human, and includes: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) relieving, alleviating or ameliorating the condition or disease or disorder or symptom thereof, such as, for example, causing regression of the condition or disease or disorder or symptom thereof.

As used herein, the term "effective amount" means that amount of a drug or a therapeutic agent or a pharmaceutical agent that will elicit the biological or medical response of a tissue, system, animal or human that is being sought, for instance, by a researcher, clinician or veterinarian.

As used herein, "pharmaceutically acceptable excipient" or "pharmaceutically acceptable carrier" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be pharmaceutically-acceptable e.g. of sufficiently high purity.

As used herein "pharmaceutically acceptable salts" means salts suitable for medical applications having a pharmaceutically acceptable anion or cation.

In one embodiment, the invention provides a method of treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, abnormal puberty, uterine fibrosis, ovarian cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian or adrenal tumor, or osteoporosis, comprising administering to a human in need thereof an effective amount of dual NK-1/NK-3 receptor antagonists or a pharmaceutically acceptable salt thereof.

In one embodiment, the invention provides a method of treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, adenomyosis, abnormal puberty, uterine fibrosis, heavy menstrual bleeding, ovarian cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian, adrenal tumor, osteoporosis, or pre-eclampsia comprising administering to a human in need thereof an effective amount of dual NK-1/NK-3 receptor antagonists or a pharmaceutically acceptable salt thereof.

In a further embodiment, the present invention provides dual NK-1/NK-3 receptor antagonists or a pharmaceutically acceptable salt thereof for use in the treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, abnormal puberty, uterine fibrosis, ovarian cancer, breast cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian or adrenal tumor, or osteoporosis, comprising administering to a human in need thereof an effective amount of dual NK-1/NK-3 receptor antagonists or a pharmaceutically acceptable salt thereof.

In a further embodiment, the present invention provides dual NK-1/NK-3 receptor antagonists or a pharmaceutically acceptable salt thereof for use in the treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, adenomyosis, abnormal puberty, uterine fibrosis, heavy menstrual bleeding, ovarian cancer, breast cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian, adrenal tumor, osteoporosis, or pre-eclampsia.

In a further aspect thereof, the invention provides the use of dual NK-1/NK-3 receptor antagonists or a pharmaceutically acceptable salt thereof for the manufacture of a medicament for the treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, abnormal puberty, uterine fibrosis, ovarian cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian or adrenal tumor, or osteoporosis.

In a further aspect thereof, the invention provides the use of a dual NK-1/NK-3 receptor antagonists or a pharmaceutically acceptable salt thereof for the manufacture of a medicament for the treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, adenomyosis, abnormal puberty, uterine fibrosis, heavy menstrual bleeding, ovarian cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian, adrenal tumor, osteoporosis, or pre-eclampsia.

In one embodiment, the sex-hormone dependent diseases according to the invention are selected from hirsutism, endometriosis, adenomyosis, uterine fibrosis, heavy menstrual bleeding, polycystic ovary syndrome (PCOS) and hot flushes.

Compounds for use herein include dual NK-1/NK-3 receptor antagonists as described in, and made according to WO2004056799, WO2004056805, WO2005002577, WO2005097794, WO2006013050, WO2007028654, WO2008128891, WO2011131571 or WO2011023733 which are incorporated herein by reference in their entirety.

Preferred pyridine derivatives of WO2006013050 for use herein are as follows:

2-(3,5-bis-trifluoromethyl-phenyl)-N-[4-(2-chloro-phenyl)-6-(2-hydroxy-ethoxy)-pyridin-3-yl]-N-methyl-isobutyramide;
2-(3,5-bis-trifluoromethyl-phenyl)-N-[4-(2-chloro-phenyl)-6-(2-hydroxy-1-hydroxymethyl-ethoxy)-pyridin-3-yl]-N-methyl-isobutyramide;
(S)-2-(3,5-bis-trifluoromethyl-phenyl)-N-[4-(4-fluoro-2-methyl-phenyl)-6-(pyrrolidin-2-ylmethoxy)-pyridin-3-yl]-N-methyl-isobutyramide;
2-(3,5-bis-trifluoromethyl-phenyl)-N-[4-(4-fluoro-2-methyl-phenyl)-6-(2-hydroxy-ethylsulfanyl)-pyridin-3-yl]-N-methyl-isobutyramide;
2-(3,5-bis-trifluoromethyl-phenyl)-N-[4-(4-fluoro-2-methyl-phenyl)-[2,3']bipyridinyl-5-yl]-N-methyl-isobutyramide;
2-(3,5-bis-trifluoromethyl-phenyl)-N-[4-(4-fluoro-2-methyl-phenyl)-1'-oxy-[2,3']bipyridinyl-5-yl]-N-methyl-isobutyramide;
2-(3,5-bis-trifluoromethyl-phenyl)-N-[4-(4-fluoro-2-methyl-phenyl)-6-(3-hydroxymethyl-phenyl)-pyridin-3-yl]-N-methyl-isobutyramide;
2-(3,5-bis-trifluoromethyl-phenyl)-N-[4-(4-fluoro-2-methyl-phenyl)-5'-hydroxymethyl-[2,3']bipyridinyl-5-yl]-N-methyl-isobutyramide;
2-(3,5-bis-trifluoromethyl-phenyl)-N-[4-(4-fluoro-2-methyl-phenyl)-2'-hydroxymethyl-[2,4']bipyridinyl-5-yl]-N-methyl-isobutyramide;
2-(3,5-bis-trifluoromethyl-phenyl)-N-[4-(4-fluoro-2-methyl-phenyl)-1'-methanesulfonyl-1',2',3',6'-tetrahydro-[2]4']bipyridinyl-5-yl]-N-methyl-isobutyramide;
2-(3,5-bis-trifluoromethyl-phenyl)-N-[4-(4-fluoro-2-methyl-phenyl)-1'-methanesulfonyl-1',2',3',4',5',6'-hexahydro-[2,4']bipyridinyl-5-yl]-N-methyl-isobutyramide;
(RS)-2-(3,5-bis-trifluoromethyl-phenyl)-N-[4-(4-fluoro-2-methyl-phenyl)-1'-methanesulfonyl-1',2',3',4',5',6'-hexahydro-[2,3]bipyridinyl-5-yl]-N-methyl-isobutyramide;
(RS)—N-[1'-acetyl-4-(4-fluoro-2-methyl-phenyl)-1,2',3',4',5',6'-hexahydro-[2,3']bipyridinyl-5-yl]-2-(3,5-bis-trifluoromethyl-phenyl)-N-methyl-isobutyramide;
2-(3,5-bis-trifluoromethyl-phenyl)-N-[6-(3,6-dihydro-2H-thiopyran-4-yl)-4-(4-fluoro-2-methyl-phenyl)-pyridin-3-yl]-N-methyl-isobutyramide;
2-(3,5-bis-trifluoromethyl-phenyl)-N-[6-(1,1-dioxo-1,2,3,6-tetrahydro-1$\lambda^6$thiopyran-4-yl)-4-(4-fluoro-2-methyl-phenyl)-pyridin-3-yl]-N-methyl-isobutyramide;
2-(3,5-bis-trifluoromethyl-phenyl)-N-[6-(1,1-dioxo-hexahydro-1$\lambda^6$-thiopyran-4-yl)-4-(4-fluoro-2-methyl-phenyl)-pyridin-3-yl]-N-methyl-isobutyramide; or pharmaceutically acceptable salts thereof.

Preferred pyrrolidine derivatives of WO2008128891 for use herein are as follows:

rac-2-(3,5-bis-trifluoromethyl-phenyl)-N-[(3S,4R)-4-(4-chloro-phenyl)-1-(morpholine-4-carbonyl)-pyrrolidin-3-yl]-N-methyl-isobutyramide;
rac-2-(3,5-dichloro-phenyl)-N-[(3S,4R)-4-(4-fluoro-phenyl)-1-(morpholine-4-carbonyl)-pyrrolidin-3-yl]-N-methyl-isobutyramide;
rac-2-(3,5-bis-trifluoromethyl-phenyl)-N-[(3S,4R)-4-(4-fluoro-2-methyl-phenyl)-1-(morpholine-4-carbonyl)-pyrrolidin-3-yl]-N-methyl-isobutyramide;
rac-2-(3,5-bis-trifluoromethyl-phenyl)-N-[(3S,4R)-4-(4-fluoro-phenyl)-1-(4-methanesulfonyl-piperazine-1-carbonyl)-pyrrolidin-3-yl]-N-methyl-isobutyramide;
rac-N-[(3S,4R)-1-(4-acetyl-piperazine-1-carbonyl)-4-(4-fluoro-phenyl)-pyrrolidin-3-yl]-2-(3,5-bis-trifluoromethyl-phenyl)-N-methyl-isobutyramide;
rac-2-(3,5-bis-trifluoromethyl-phenyl)-N-[(3S,4R)-1-(4-methanesulfonyl-piperazine-1-carbonyl)-4-phenyl-pyrrolidin-3-yl]-N-methyl-isobutyramide;
rac-2-(3,5-dichloro-phenyl)-N-[(3S,4R)-4-(4-fluoro-phenyl)-1-(4-methanesulfonyl-piperazine-1-carbonyl)-pyrrolidin-3-yl]-N-methyl-isobutyramide;
rac-2-(3,5-bis-trifluoromethyl-phenyl)-N-[(3S,4R)-4-(4-fluoro-2-methyl-phenyl)-1-(4-methanesulfonyl-piperazine-1-carbonyl)-pyrrolidin-3-yl]-N-methyl-isobutyramide;
rac-N-[(3S,4R)-4-(4-chloro-phenyl)-1-(4-methanesulfonyl-piperazine-1-carbonyl)-pyrrolidin-3-yl]-2-(3,5-dichloro-phenyl)-N-methyl-isobutyramide;
rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid bis-(2-hydroxy-ethyl)-amide;
rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid (2-hydroxy-ethyl)-amide;
or pharmaceutically acceptable salts thereof.

Preferred pyrazolopyridine derivatives of WO2011131571 for use herein are as follows:

2-(3,5-bis-trifluoromethyl-phenyl)-N-(1-ethyl-4-o-tolyl-1H-pyrazolo[3,4-b]pyridin-5-yl)-N-methyl-isobutyramide;
2-(3,5-bis-trifluoromethyl-phenyl)-N-[1-ethyl-4-(4-fluoro-2-methyl-phenyl)-1H-pyrazolo[3,4-b]pyridin-5-yl]-N-methyl-isobutyramide;
2-(3,5-bis-trifluoromethyl-phenyl)-N-[4-(2-chloro-phenyl)-1-ethyl-1-H-pyrazolo[3,4-b]pyridin-5-yl]-N-methyl-isobutyramide;
2-(3,5-bis-trifluoromethyl-phenyl)-N-[4-(3,4-dichloro-phenyl)-1-ethyl-1H-pyrazolo[3,4-]pyridin-5-yl]-N-methyl-isobutyramide;
2-(3,5-bis-trifluoromethyl-phenyl)-N-[1-(2,2-difluoro-ethyl)-4-(4-fluoro-2-methyl-phenyl)-1H-pyrazolo[3,4-b]pyridin-5-yl]-N-methyl-isobutyramide;
2-(3,5-bis-trifluoromethyl-phenyl)-N-[4-(4-fluoro-2-methyl-phenyl)-1-methyl-1H-pyrazolo[3,4-b]pyridin-5-yl]-N-methyl-isobutyramide;
N-[1-benzyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;
2-(3,5-bis-trifluoromethyl-phenyl)-N-[1-ethyl-4-(4-fluoro-2-methoxy-phenyl)-1H-pyrazolo[3,4-b]pyridin-5-yl]-N-methyl-isobutyramide;
2-(3,5-bis-trifluoromethyl-phenyl)-N-[4-(2-chloro-3-fluoro-phenyl)-1-ethyl-1H-pyrazolo[3,4-b]pyridin-5-yl]-N-methyl-isobutyramide;
2-(3,5-bis-trifluoromethyl-phenyl)-N-[4-(2,3-dichloro-phenyl)-1-ethyl-1H-pyrazolo[3,4-b]pyridin-5 yl]-N-methyl-isobutyramide;

2-(3,5-bis-trifluoromethyl-phenyl)-N-[4-(2-chloro-4-fluoro-phenyl)-1-ethyl-1H-pyrazolo[3,4-b]pyridin-5-yl]-N-methyl-isobutyramide;

2-(3,5-bis-trifluoromethyl-phenyl)-N-[4-(2-chloro-5-hydroxymethyl-phenyl)-1-ethyl-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

N-[1-acetyl-4-(4-fluoro-2-methyl-phenyl)-1H-pyrazolo[3,4-b]pyridin-5-yl]-2-(3,5-bis-trifluoromethyl-phenyl)-N-methyl-isobutyramide;

2-(3,5-bis-trifluoromethyl-phenyl)-N-[4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-(2-methoxy-acetyl)-1H-pyrazolo[3,4-b]pyridin-5-yl]-N-methyl-isobutyramide;

2-(3,5-bis-trifluoromethyl-phenyl)-N-[1-cyclopropanecarbonyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methanesulfonyl-1H-pyrazolo[3,4-b]pyridin-5-yl]-N-methyl-isobutyramide;

2-(3,5-bis-trifluoromethyl-phenyl)-N-[1-dimethylsulfamoyl-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methanesulfonylmethyl-1H-pyrazolo[3,4-b]pyridin-5-yl]-N-methyl-isobutyramide;

2-(3,5-bis-trifluoromethyl-phenyl)-N-[1-ethyl-4-(4-methyl-thiophen-3-yl)-1H-pyrazolo[3,4-b]pyridin-5-yl]-N-methyl-isobutyramide;

2-(3,5-bis-trifluoromethyl-phenyl)-N-[4-(2-chloro-thiophen-3-yl)-1-ethyl-1H-pyrazolo[3,4-b]pyridin-5-yl]-N-methyl-isobutyramide;

2-(3-fluoro-5-trifluoromethyl-phenyl)-N-[1-ethyl-4-(4-fluoro-2-methyl-phenyl)-1H-pyrazolo[3,4-b]pyridin-5-yl]-N-methyl-isobutyramide; or 2-(3,5-dichloro-phenyl)-N-[1-ethyl-4-(4-fluoro-2-methyl-phenyl)-1H-pyrazolo[3,4-b]pyridin-5-yl]-N-methyl-isobutyramide;

or pharmaceutically acceptable salts thereof.

Particularly preferred compounds for use herein are

2-[3,5-Bis(trifluoromethyl)phenyl]-N-{4-(4-fluoro-2-methylphenyl)-6-[(7S,9aS)-7-(hydroxylmethyl)hexahydropyrazino[2,1-c][1,4]oxazin-8(1H)-yl]-3-pyridinyl}-N,2-dimethylpropanamide;

(2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl-isobutyramide;

2-(3,5-bis-trifluoromethyl-phenyl)-N-[4-(4-fluoro-2-methyl-phenyl)-1'-methanesulfonyl-1',2',3',6'-tetrahydro-[2)4']bipyridinyl-5-yl]-N-methyl-isobutyramide;

2-(3,5-bis-trifluoromethyl-phenyl)-N-[4-(4-fluoro-2-methyl-phenyl)-1'-methanesulfonyl-1',2',3',4',5,6-hexahydro-[2,4']bipyridinyl-5-yl]-N-methyl-isobutyramide;

2-(3,5-bis-trifluoromethyl-phenyl)-N-[6-(1,1-dioxo-1,2,3,6-tetrahydro-1$\lambda^6$thiopyran-4-yl)-4-(4-fluoro-2-methyl-phenyl)-pyridin-3-yl]-N-methyl-isobutyramide;

rac-N-[(3S,4R)-4-(4-chloro-phenyl)-1-(4-methanesulfonyl-piperazine-1-carbonyl)-pyrrolidin-3-yl]-2-(3,5-dichloro-phenyl)-N-methyl-isobutyramide;

2-(3,5-bis-trifluoromethyl-phenyl)-N-[1-(2,2-difluoro-ethyl)-4-(4-fluoro-2-methyl-phenyl)-1H-pyrazolo[3,4-b]pyridin-5-yl]-N-methyl-isobutyramide;

2-(3,5-bis-trifluoromethyl-phenyl)-N-[4-(4-fluoro-2-methyl-phenyl)-1-methanesulfonylmethyl-1H-pyrazolo[3,4-b]pyridin-5-yl]-N-methyl-isobutyramide;

or pharmaceutically acceptable salts thereof.

Particularly preferred compounds according to the invention are

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (formula A);

(A)

(2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl-isobutyramide (formula B);

(B)

or pharmaceutically acceptable salt or crystalline forms thereof.

Methods for preparing compound of formula A, salts thereof and its crystalline forms are described in WO2007028654 and WO2011023733 respectively, which methods are incorporated herein by reference.

Specifically WO2011023733 discloses compound of formula A in a crystalline anhydrate form (Form 1), having certain characteristic 2 theta angles occurring at 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å).

Methods for preparing the compound of formula B or salt thereof are described in WO2005002577, which methods are incorporated herein by reference.

In a further embodiment, the invention provides
2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide or (2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl-isobutyramide; pharmaceutically acceptable salts or crystalline forms thereof for use for the treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, adenomyosis, abnormal puberty, uterine fibrosis, heavy menstrual bleeding, ovarian cancer, breast cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian, adrenal tumor, osteoporosis, or pre-eclampsia.

In a further embodiment, the invention provides a method of treatment of sex-hormone dependent diseases selected from the group consisting of benign prostatic hyperplasia (BPH), metastatic prostatic carcinoma, testicular cancer, breast cancer, androgen dependent acne, seborrhoea, hirsutism, hypertrichosis, male pattern baldness, female androgenetic alopecia, endometriosis, adenomyosis, abnormal puberty, uterine fibrosis, heavy menstrual bleeding, ovarian cancer, breast cancer, hyperandrogenism, virilization, polycystic ovary syndrome (PCOS), HAIR-AN syndrome, ovarian hyperthecosis, hidradenitis suppurativa, hot flushes and precocious puberty in boys, follicular maturation arrest, atresia, anovulation, dysmenorrhea, dysfunctional uterine bleeding, infertility virilizing ovarian, adrenal tumor, osteoporosis or pre-eclampsia which comprises administering to a human in need thereof an effective amount of the compounds:

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide;

(2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl isobutyramide; or pharmaceutically acceptable salts or crystalline forms thereof.

In a further embodiment, the invention provides a method of treatment of sex-hormone dependent diseases selected from the group consisting of androgen dependent hirsutism, female androgenetic, endometriosis, adenomyosis, uterine fibrosis, heavy menstrual bleeding, polycystic ovary syndrome (PCOS) and hot flushes, which comprises administering to a human in need thereof an effective amount comprising administering to a human in need thereof an effective amount of dual NK-1/NK-3 receptor antagonists or a pharmaceutically acceptable salt thereof.

In a further embodiment, the invention provides a method of treatment of sex-hormone dependent diseases selected from the group consisting of androgen dependent hirsutism, female androgenetic endometriosis, adenomyosis, uterine fibrosis, heavy menstrual bleeding, polycystic ovary syndrome (PCOS) and hot flushes, which comprises administering to a human in need thereof an effective amount of 2-[3,5-Bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide;

(2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl-isobutyramide; or pharmaceutically acceptable salts thereof.

In one embodiment, the compound according to the invention is 2-[3,5-Bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide or crystalline anhydrate forms thereof for use in the treatment of hirsutism, endometriosis, adenomyosis, uterine fibrosis, heavy menstrual bleeding, polycystic ovary syndrome (PCOS) and hot flushes.

In a yet further embodiment, the compound according to the invention is 2-[3,5-Bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl)}-N,2-dimethylpropanamide as anhydrous crystalline Form 1 for use in the treatment of endometriosis, adenomyosis, uterine fibrosis, heavy menstrual bleeding, polycystic ovary syndrome (PCOS) and hot flushes.

In a yet further embodiment, the compound according to the invention is 2-[3,5-Bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide as anhydrous crystalline Form 1 for use in the treatment of hot flushes.

Owing to their activity on the gonadotropin-releasing hormone (GnRH) pathway, dual NK-1/NK-3 receptor antagonists can be used alone or in combination with estrogen and progestin as contraceptives.

Thus, in a further aspect, the present invention provides a method for providing oral contraception, said method comprising administering to the patient an effective amount of dual NK-1/NK-3 receptor antagonists.

In a further aspect of the invention there is provided the use of dual NK-1/NK-3 receptor antagonists for the production of a drug for oral contraception.

Compounds for use for oral contraception include dual NK-1/NK-3 receptor antagonists as described in, and made according to WO2004056799, WO2004056805, WO2005002577, WO2005097794, WO2006013050, WO2007028654, WO2008128891, WO2011131571, WO2011023733 which are incorporated herein by reference in their entirety.

Preferred pyridine derivatives of WO2006013050 for use for oral contraception are those disclosed from line 28 of page 8 to line 24 of page 9 respectively of the present specification.

Preferred pyrrolidine derivatives of WO2008128891 for use for oral contraception are those disclosed from line 26 of page 9 to line 9 of page 10 of the present specification.

Preferred pyrazolopyridine derivatives of WO201131571 for use for oral contraception are those disclosed from line 11 of page 10 to line 20 of page 11 of the present specification.

Particularly preferred compounds for use for oral contraception are

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (Formula A);

(A)

(2R,3S)-2-(3,5-bis-trifluoromethylphenyl)-N-[4-(4-fluoro-2-methyl-phenyl)-6-(3-hydroxy-2-hydroxymethyl-pyrrolidin-1-yl)-pyridin-3-yl]-N-methyl-isobutyramide (Formula B);

(B)

or pharmaceutically acceptable salt or crystalline forms thereof.

The present invention further provides a pharmaceutical composition comprising a dual NK-1/NK-3 receptor antagonist or a compound described above, a pharmaceutically acceptable salt or crystalline forms thereof, and a pharmaceutically acceptable carrier.

Thus, in one embodiment, the invention provides a pharmaceutical composition comprising a dual NK-1/NK-3 receptor antagonist or a pharmaceutically acceptable salt thereof, and a pharmaceutically acceptable carrier, for use in the treatment of sex hormone-dependent diseases.

In a further embodiment, the invention provides a pharmaceutical composition comprising 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide or crystalline anhydrate forms thereof and a pharmaceutically acceptable carrier for use in the treatment of sex hormone-dependent diseases.

In a further embodiment, the invention provides a pharmaceutical composition comprising 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide or crystalline anhydrate forms thereof and a pharmaceutically acceptable carrier for use in the treatment hirsutism, endometriosis, adenomyosis, uterine fibrosis, heavy menstrual bleeding, polycystic ovary syndrome (PCOS) and hot flushes.

In a further embodiment, the present invention provides a drug containing a dual NK-1/NK-3 receptor antagonist and a pharmaceutically acceptable carrier.

In a yet further embodiment, the present invention provides a drug containing 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide or a pharmaceutically acceptable salts thereof and a pharmaceutically acceptable carrier.

Such a medicament, and a composition of this invention, may be prepared by admixture of a compound of the invention with an appropriate pharmaceutically acceptable carrier. It may contain a diluent, binder, filler, disintegrant, flavoring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarian fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage.

Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl-pyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers.

When the composition is in the form of a tablet, powder, or lozenge, any carrier suitable for formulating solid pharmaceutical compositions may be used, examples being magnesium stearate, starch, glucose, lactose, sucrose, rice flour and chalk.

Tablets may be coated according to methods well known in normal pharmaceutical practice, in particular with an enteric coating. The composition may also be in the form of an ingestible capsule, for example of gelatine containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatine, hydroxyethylcellulose, carboxymethylcellulose, aluminum stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavoring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e. g. sterile pyrogenic-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives.

Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronized compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilizing a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

The manufacture of the pharmaceutical compositions according to the present subject matter may be performed according to methods known in the art. Commonly known and used pharmaceutically acceptable auxiliaries as well as further suitable diluents, flavourings, sweetening agents, colouring agents etc. may be used, depending on the intended mode of administration as well as particular characteristics of the active compound to be used, such as solubility, bioavailability etc.

Any non-toxic, inert, and effective topical, oral, etc. pharmaceutically acceptable carrier may be used to formulate the compositions described herein.

Well-known carriers used to formulate other topical therapeutic compositions for administration to humans are useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug.

As mentioned above, the effective dose of compound depends on the particular compound employed, the condition of the patient and on the frequency and route of administration. An effective dose will generally contain from 1 mg to 250 mg and preferably will contain from 10 mg to 220 mg, in particular 30 mg to 200 mg.

The composition may be administered once or more times a day for example 2, 3 or 4 times daily, and the total daily dose for a 70 kg adult will normally be in the range 30 mg to 200 mg.

Alternatively the unit dose will contain from 10 to 100 mg of active ingredient and be administered in multiples, if desired, to give the preceding daily doses.

No unacceptable toxicological effects are expected with compounds of the invention when administered in accordance with the invention.

The compounds of the invention or pharmaceutically acceptable salts thereof and the other pharmaceutically active agent(s) may be administered together in a fix combination or separately (i.e. non fix combination).

When administered separately, this may occur separately or sequentially in any order and treatment regimens in which the agents are not necessarily administered by the same route of administration may also occur. The amounts of the compound inventions or pharmaceutically acceptable salts thereof and the other pharmaceutically active agent(s) and the relative timings of administration will be selected in order to achieve the desired combined therapeutic effect.

Examples of suitable therapeutic agents which may be used in combination of the compounds of the invention or pharmaceutically acceptable salts thereof include agonists of Gonadotropin-releasing hormone (GnRH) such as nafarelin, buserelin, goserelin and leuprorelin; antagonists of the Gonadotropin-releasing hormone (GnRH) such as degarelix, ganirelix, cetrorelix, abarelix and elagolix; 5-alpha-reductase inhibitors such as dutasteride and finasteride; combined androgen receptor antagonists/5-alpha-reductase inhibitors such as spironolactone; anti-androgens such as cyproterone acetate and flutamide; combined (estrogen with a progestin) oral contraceptives such as estrogen with either norgestimate, or norethindrone, or drospirenone; progesterone receptor modulators such as ulipristal acetate.

Biological Data

The anti-androgenic effects of the compounds useful herein are determined by the following clinical studies on human volunteers which demonstrate testosterone lowering effects.

Example 1

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (hereinafter Compound A) was administered both as single and repeat ascending doses in male human volunteers (HV) and the effect of Compound A on the levels of testosterone was assessed.

1. Single Ascending Dose Studies

Male HVs received in a single-blinded, randomised fashion, single ascending oral doses of placebo or Compound A ranging from 10 to 250 mg as suspensions.

Figure 1:
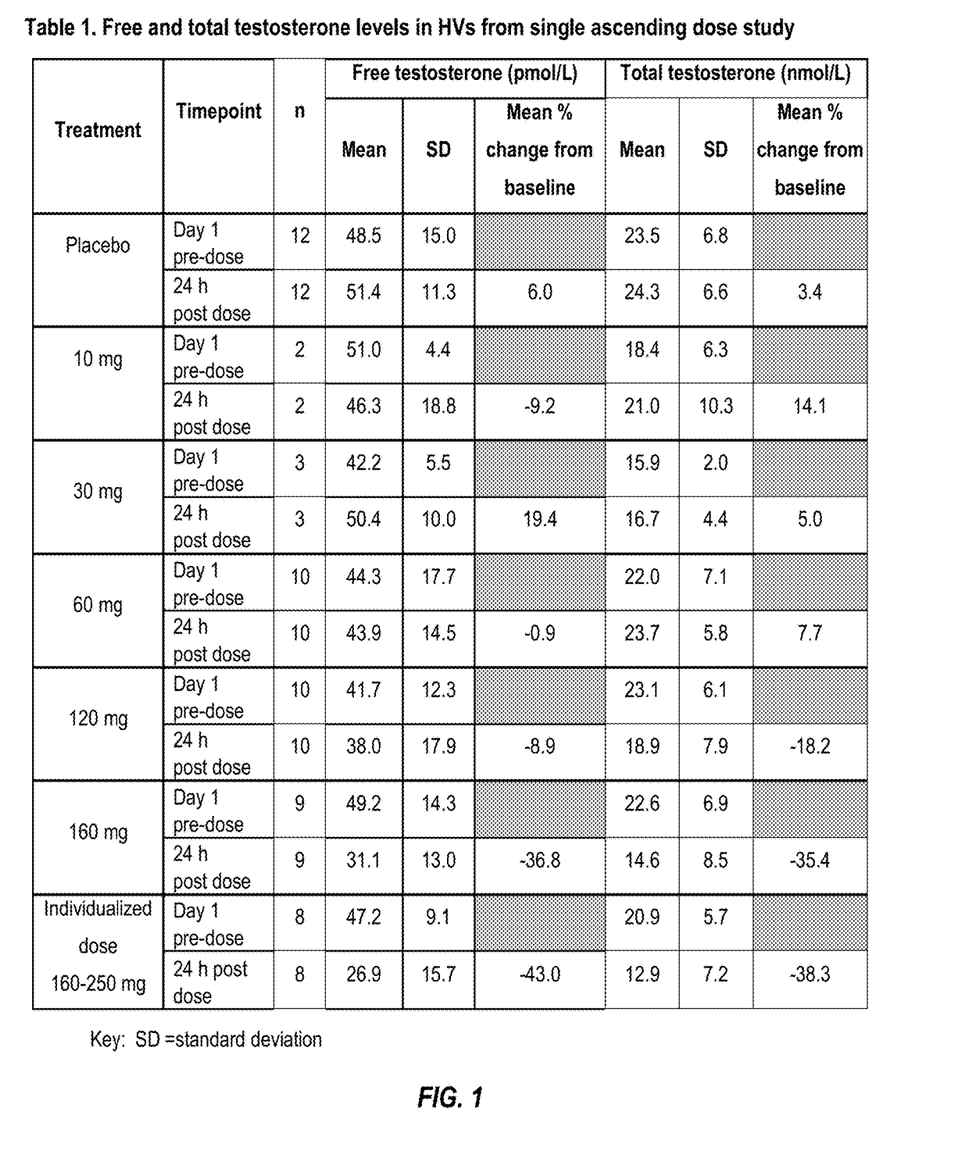
FIG. 1 contains Table 1, which reports the free and total testosterone levels in male human volunteers (HVs) from a single ascending dose study.

Free and total testosterone serum levels were measured at Day-1, then 24 hours after each dose and at follow-up (7-14 days after Compound A dose). Resulting HV serum testosterone levels (free and total) were determined as described in Table 1 (FIG. 1).

As shown in Table 1 (FIG. 1) clinically relevant reductions in free and total testosterone levels are evident within 24 h following administration of Compound A. At doses of ≥160 mg the decreases range from between 35% and 43%. Testosterone levels recovered to baseline levels at follow-up (7-14 days after the last dose of Compound A).

2. Repeat Ascending Dose of Compound A

Part A of this study comprised 3 cohorts that investigated the safety, tolerability and PK of escalating multiple daily doses of Compound A. Information on these cohorts is as follows:

Cohorts 1 and 2 received Compound A for 14 days; with a follow-up 7 to 14 days after their last dose. Testosterone levels in both cohorts were measured pre-dose on Day 1, on Day 15 and at follow-up.

Cohort 3 also received Compound A over a repeat treatment period of 14 days; with a follow-up 7-14 days after their last dose. Testosterone levels were measured in this cohort pre-dose on Day-1 and pre-dose on Day 14, and at follow-up.

Figure 2:
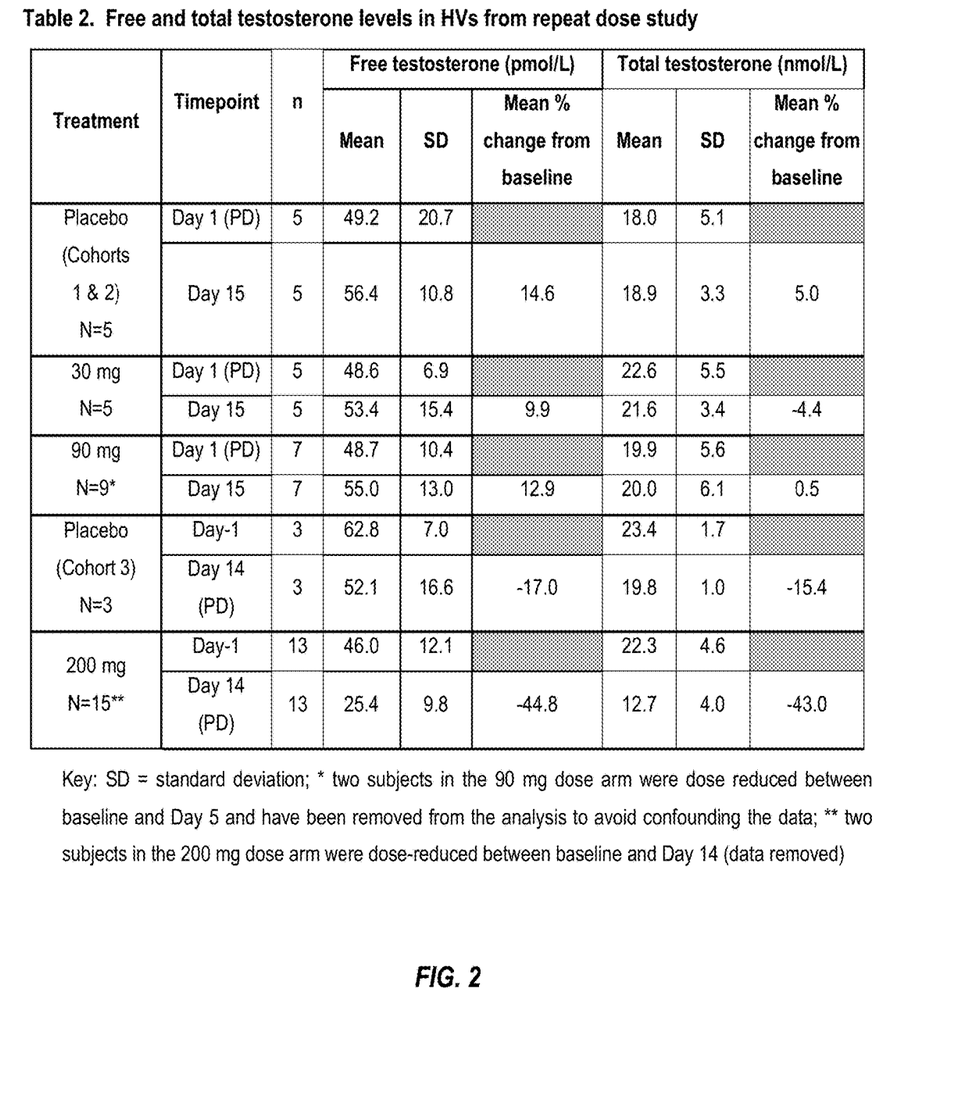
FIG. 2 contains Table 2, which reports the free and total testosterone levels in HVs from a repeat dose study.

Resulting HV serum testosterone levels (free and total) were determined as described in Table 2 (FIG. 2).

Clinically relevant reductions in free and total testosterone levels were again evident after repeat dosing with Compound A. At doses of 200 mg after 14 days; the decreases ranged from between 43% and 45%; consistent with the values observed after 24 hours in the single ascending dose study. Testosterone levels recovered to baseline levels at follow-up (7-14 days after the last dose of 200 mg Compound A).

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent Therefore the Examples herein are to be construed as merely illustrative and not a limitation of the scope of the present invention in any way. The embodiments of the invention in which an exclusive property or privilege is claimed are defined as follows.

The invention claimed is:

1. A method of treatment of hot flushes comprising administering to a human in need thereof an effective amount of dual NK-1/NK-3 receptor antagonist 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide of formula (A) or a pharmaceutically acceptable salt thereof 2. A method according to claim 1, wherein the dual NK-1/NK-3 receptor antagonist is the compound of formula (A) as crystalline anhydrate Form 1.

3. A method of treatment of hot flushes comprising:
orally administering to a human in need thereof an effective amount of dual NK-1/NK-3 receptor antagonist 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide of formula (A) or a pharmaceutically acceptable salt thereof wherein said orally administering is effective to alleviate symptoms of hot flushes.

4. A method according to claim 3, wherein the dual NK-1/NK-3 receptor antagonist is the compound of formula (A) as crystalline anhydrate Form 1.

* * * * *

UNITED STATES PATENT AND TRADEMARK OFFICE
CERTIFICATE OF CORRECTION

PATENT NO. : 10,195,205 B2                                    Page 1 of 4
APPLICATION NO. : 15/157430
DATED : February 5, 2019
INVENTOR(S) : Mike Trower It is certified that error appears in the above-identified patent and that said Letters Patent is hereby corrected as shown below:

In the Specification

At Column 10, Line number 10, please delete:

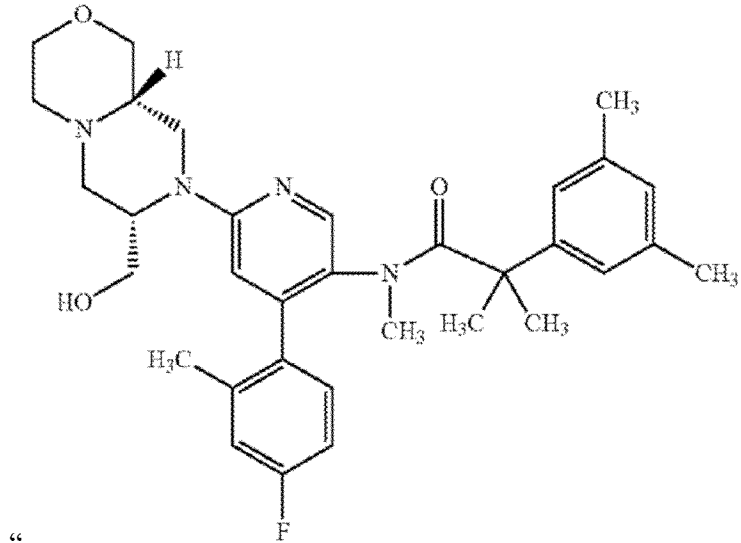

"                                                                      "

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,195,205 B2

And insert:

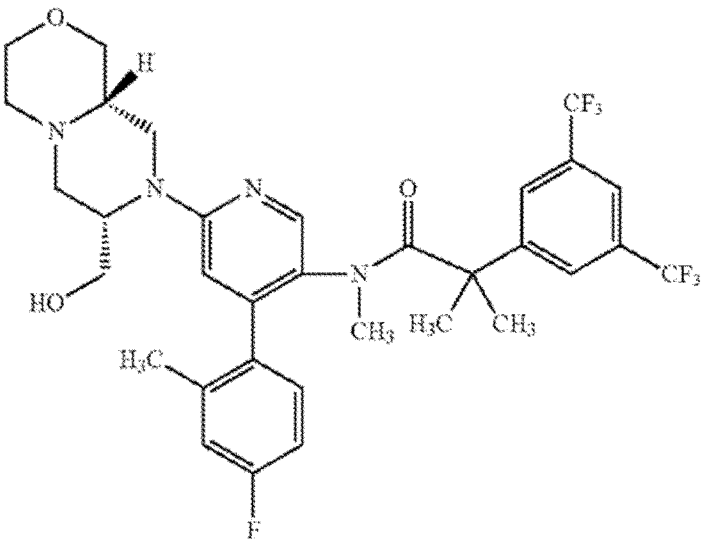

(A)

--                                                                                             --.

At Column 13, Line number 1, please delete:

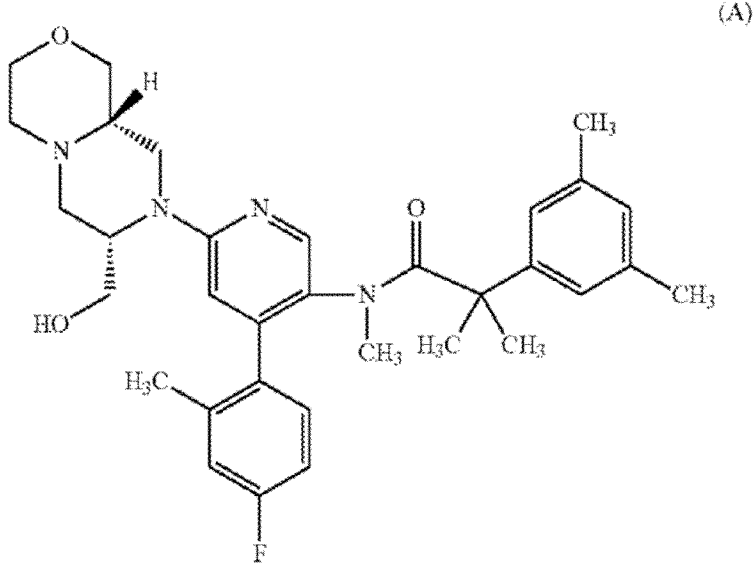

(A)

"                                                                                              "

And insert:
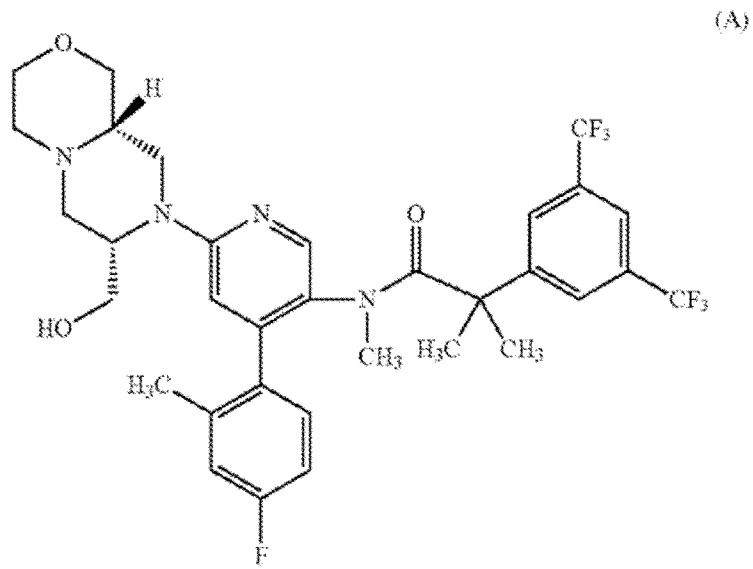
--                                                                              --.
In the Claims
At Column 18, Line number 5, Claim number 1, please delete:
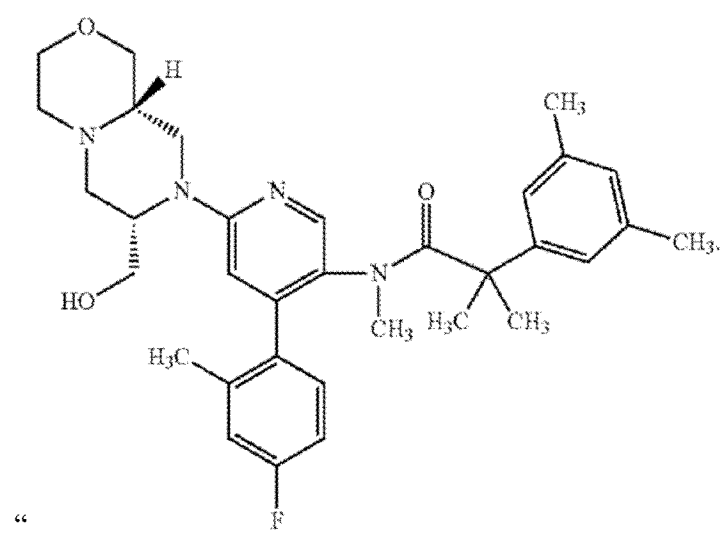
"                                                                              "

CERTIFICATE OF CORRECTION (continued)
U.S. Pat. No. 10,195,205 B2

Page 4 of 4

And insert:

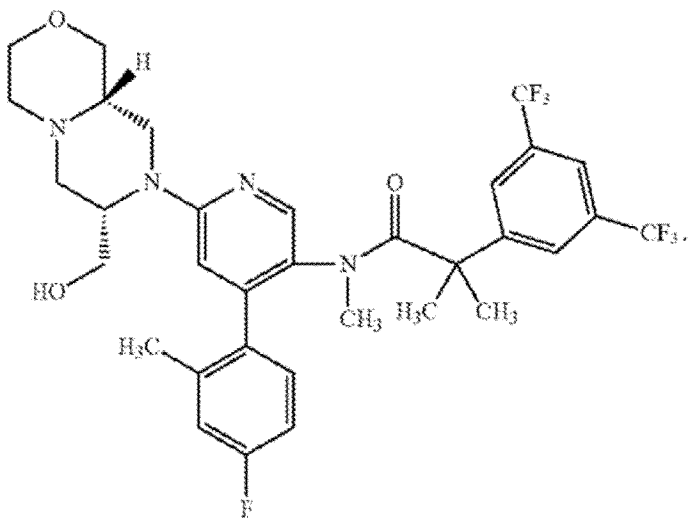

--                                    --.